United States Patent
Lundberg et al.

(10) Patent No.: US 7,270,638 B2
(45) Date of Patent: Sep. 18, 2007

(54) METHOD AND DEVICE FOR DIAGNOSIS USING AN OSCILLATING AIRFLOW

(75) Inventors: Jon Lundberg, Danderyd (SE); Eddie Weitzberg, Stockholm (SE)

(73) Assignee: Aerocrine AB, Solna (SE)

( * ) Notice: Subject to any disclaimer, the term of this patent is extended or adjusted under 35 U.S.C. 154(b) by 259 days.

(21) Appl. No.: 10/496,897

(22) PCT Filed: Jan. 31, 2003

(86) PCT No.: PCT/SE03/00175

§ 371 (c)(1),
(2), (4) Date: Jan. 7, 2005

(87) PCT Pub. No.: WO03/063703

PCT Pub. Date: Aug. 7, 2003

(65) Prior Publication Data

US 2005/0143673 A1    Jun. 30, 2005

(30) Foreign Application Priority Data

Feb. 1, 2002    (SE) ................................. 0200300

(51) Int. Cl.
*A61B 5/08* (2006.01)
(52) U.S. Cl. ...................... 600/532; 600/529
(58) Field of Classification Search ......... 600/529–543
See application file for complete search history.

(56) References Cited

U.S. PATENT DOCUMENTS

| | | | |
|---|---|---|---|
| 5,318,038 A * | 6/1994 | Jackson et al. | 600/533 |
| 5,454,375 A * | 10/1995 | Rothenberg | 600/538 |
| 5,922,610 A | 7/1999 | Alving et al. | |
| 6,138,675 A | 10/2000 | Berthon-Jones | |
| 6,142,952 A | 11/2000 | Behbehani et al. | |
| 6,557,554 B1 * | 5/2003 | Sugiura | 128/204.18 |

FOREIGN PATENT DOCUMENTS

RU    1836050    8/1999

OTHER PUBLICATIONS

Weitzberg, Eddie et al. "Humming Greatly Increases Nasal Nitric Oxide" *Am J Respir Crit Care Med*, vol. 166: 144-145, 2002.
International Search Report mailed on Apr. 29, 2003, for PCT patent application No. PCT/SE03/00175 filed on Jan. 31, 2003, 6 pages.

* cited by examiner

*Primary Examiner*—Charles A. Marmor, II
*Assistant Examiner*—Karen E Toth
(74) *Attorney, Agent, or Firm*—Morrison & Foerster LLP (57) ABSTRACT

It has surprisingly been found that nasal NO release is greatly increased by the presence of a an oscillating airflow in healthy subjects. Accordingly, a device comprising means for generating and/or maintaining an oscillating airflow is described and suggested for use in the diagnosis of a condition of the upper airways of a human. The invention also encompasses method wherein the concentration and/or flow of at least one gaseous component in nasally exhaled air is determined and recorded in the presence and absence of an oscillating airflow acting on the upper airways or parts thereof.

29 Claims, 8 Drawing Sheets

METHOD AND DEVICE FOR DIAGNOSIS USING AN OSCILLATING AIRFLOW

This application is a U.S. national phase application of International PCT/SE03/00175, filed Jan. 31, 2003, which claims priority to Swedish Patent Application No. 0200300-2 filed Feb. 1, 2002, all of which are hereby incorporated by reference in their entirety.

The present invention relates to the investigation of the upper airways of a human, and in particular to a device and a method for use in the determination of the function and status of the sinuses, as well as for use as an aid in the diagnosis of various diseases of the human upper airways.

BACKGROUND OF THE INVENTION

The paranasal sinuses are cavities inside the facial bones surrounding the nose, which communicate with the nasal cavity through narrow ostia. The mucous membrane of the sinus is continuous with that of the nasal cavity. The maxillary sinuses constitute the largest of these cavities. An opening in the medial wall of the maxillary sinus communicates with the middle meatus of the nose. Obstruction of the sinus ostium is a central event in the pathogenesis of sinusitis.

The gas nitric oxide (NO) is released in the human respiratory tract. The major part of the NO found in exhaled air originates in the nasal airways and this NO can be measured non-invasively with different sampling techniques. It is known that a large production of NO takes place in the parnasal sinuses where an inducible NO synthase is constantly expressed in the epithelial cells. NO is released also from other sources in the nose e.g. the nasal mucosa. However, the relative contribution from the different NO sources in the upper airways to the NO found in nasal air is difficult to estimate. The sinuses communicate with the nasal cavity through ostia and the rate of gas exchange between these cavities is dependent e.g. on the size of the ostia A patent ostium is essential for maintenance of sinus integrity. Blockage of the ostium, e.g. caused by virus-induced mucosal swelling, results in decreased oxygen tension, mucosal edema, reduced mucociliary transport and eventually bacterial colonisation. Earlier studies have shown that nasal NO levels are markedly decreased in airway disorders affecting the sinuses, e.g. primary ciliary dyskinesia (PCD) and cystic fibrosis (CF). The concentrations of NO in the healthy sinuses are very high, sometimes more than 20 ppm.

Sinusitis is a very common disease causing much human suffering and enormous costs for the society. The self-reported prevalence of chronic sinusitis in the USA is about 12% of the population. There are several problems involved in the diagnosis and treatment of this disorder. For example, headache, rhinorrhea and nasal congestion are extremely common, but these symptoms do not necessarily imply sinusitis. Therefore the true incidence of sinusitis is lower.

Proper ventilation of the sinuses is essential for sinus integrity. In fact, occlusion of the ostia is considered the key factor in the pathogenesis of sinusitis. Such occlusion may be of mechanical or mucosal origin i.e. septum deviation, nasal polyposis, allergic rhinitis or most commonly an acute viral infection. The basic principles of treatment are to cure any infection present and to promote sinus drainage both during and after treatment to prevent recurrence. Antibiotics remain the cornerstone treatment in medical handling of acute infectious sinusitis. In addition, medical intervention with nasal decongestants as well as surgical treatment is frequently used in prevention and treatment of chronic sinusitis with the purpose of improving sinus drainage.

PRIOR ART

U.S. Pat. No. 6,142,952 describes a method and apparatus for detection and diagnosis of airway obstruction. The invention of the '952 patent is directed towards pressure and flow data measurements of pressurized breathable gas supplied to the patient's airways with an oscillation component or forced probing signal. The gas is supplied with an interface including a mask and a flexible hose and the oscillating component or forced probing signal with a loudspeaker coupled to a frequency generator. Pressure and flow of the breathable gas in the interface are measured or sampled to obtain characteristics of the patient's airway.

An experimental model for the study of gas exchange through the ostium of the maxillary sinus has been developed (Aust, R., and Drettner, B., *Uppsala J Med Sci,* 79; 177-186, 1974). In their article, Aust and Drettner first refer to previously known methods involving the introduction of a small electrode for $pO_2$-measurements into the maxlary sinus and a continuous recording of the oxygen content in the sinus. Aust and Drettner instead developed an experimental model using a rubber nose, moulded from a cadaver, and a nitrogen filled syringe representing the maxillary sinus. An air stream through the nasal model was generated by a respirator, and the pressure changes in the syringe were recorded. As a measure of the gas exchange taking place, the oxygen content in the syringe was measured. The respiratory frequency was constant in all model experiments, whereas the volume of the syringe and the diameter at the connection between the nasal model and the syringe could be varied. The volume of the syringe represented the volume of the maxillary sinus, and the diameter at the connection the diameter of the ostia The results indicated that the gas exchange is dependent of the diameter of the ostia.

In another article (Aust, R. and Drettner, B., *Acta Otolaryng* 78:432-435, 1974) a method for measuring the functional size of the maxillary ostium in living patients is described. The method is based on the measurement of the pressure rise in a maxillary ostium with patent ostium caused by an air stream led into the sinus through a cannula entering the antrum through the lower nasal meatus.

Still earlier methods for studying the patency of the maxillary ostium relied on the recording of the pressure in both the nasal canal and the maxillary sinus during breathing, blowing and sniffing.

A noninvasive test is the 133-xenon washout technique in which a mixture of air and 133-xenon is insufflated into the nasal cavities (Paulsson et al., *Ann. Otol. Rhinol. Laryngol.,* 2001; 110:667-74). The passage into the sinuses is facilitated by increasing pressure obtained by the subjects inflating a balloon. The washout of 133-xenon is monitored by a scintillation camera allowing single photon emission computed tomography (SPECT). The washout halftimes are used as a measure of the ventilation of the sinuses.

The invasive tests are potentially painful for the patients and cumbersome to perform. They are therefore not suitable for use in daily clinical practice. A easy non-invasive test that could be used to measure sinus ostial patency would be most useful. Such test could help to identify subjects at risk of developing sinusitis. Also, it could be used to monitor effects of surgical or medical interventions aimed for prevention of sinusitis.

SUMMARY OF THE INVENTION

The above problems are solved by a device according to the present invention, for use in the analysis of the condition of the upper airways of a human, in particular the condition of the sinus or sinuses of a human, wherein said device comprises means for generating and/or maintaining an oscillating airflow acting on the upper airways or parts thereof and is suitable for connection to means for determining and recording the concentration and/or flow of a gas present in the exhaled air of the human. Another aspect of the invention is a method for use as an aid in the investigation of the upper airways of a human, in particular for the analysis of the condition of the sinus or sinuses of a human, wherein the concentration and/or flow of at least one gaseous component in nasally exhaled air is determined and recorded in the presence and absence of an oscillating airflow. Further features and associated advantages of the present invention will be evident from the description, examples and claims, incorporated herein by reference.

SHORT DESCRIPTION OF THE DRAWINGS

The invention will be disclosed in closer detail in the following description, and examples, with reference to the attached drawings in which.

DESCRIPTION

The present inventors have surprisingly found that nasal NO release is greatly increased by the presence of an oscillating airflow in healthy subjects. This increase likely reflects an increased contribution of NO from the paranasal sinuses. Measurement of nasal NO in the presence of an oscillating airflow is an easy non-invasive test that can give valuable information about the condition of the upper airways, e.g. the NO production in the sinuses as well as sinus ostial function.

An external source of an oscillating airflow or a humming sound generated by the human under study causes the air to oscillate which in turn seems to increase the exchange of air between the sinuses and the nasal cavity. This was also confirmed in the two-compartment model system where an oscillating airflow simulating that achieved by humming resulted in a great increase in NO levels. The volume in the syringe, the NO concentration as well as the diameter of the syringe tip (representing the sinus ostium) were chosen to resemble physiological values for these parameters. The normal size of an ostium is approximately 2.4 mm. Interestingly, NO levels were found to be strongly dependent on the diameter of the syringe tip. This shows that the increase in nasal NO during in vivo humming or in the presence of an oscillating airflow is dependent on ostial size. In addition, sinus NO concentrations and humming frequency were shown to affect sinus ventilation. It is possible that several other factors will influence the rate of exchange between the two cavities.

Surprisingly, topical administration of a NOS inhibitor in the nose reduced nasal NO output by more than 50% during quiet breathing but had no effect on the increase in nasal NO during humming. Again, this supports the notion that this increase is due to enhanced ventilation of the sinuses, which are not reached by topical nasal sprays. The present inventors cannot exclude that humming increases NO release also from other sources within the nose. For example the oscillating airflows may generally increase the release of NO solved in the epithelial cells and fluid linings. However, as shown in the experiments below, a suggested method could be to start with repeated humming maneuvers to empty the sinuses, immediately followed by a silent nasal exhalation along with NO measurements. In this way sinus contribution to nasally exhaled NO would be minimized which could help to unmask changes in nasal mucosal NO output.

Based on the above findings, confirmed in both in vivo studies, and in an experimental set-up, the inventors make available a device for use in the analysis of the upper airways, and in particular for determining the condition of the sinus or sinuses of a human, wherein said device comprises means for generating and/or maintaining an oscillating airflow having a frequency, duration and flow sufficient to enhance the ventilation of the sinuses, said device being suitable for connection to means for determining and recording the concentration and/or flow of a gas present in the exhaled air of said human being. In one embodiment of the invention the gas is endogenous NO.

In this context it is understood that the term "upper airways" refers to the airways located above the vocal cords, including the paranasal sinuses, nasal cavity, nasopharynx, epipharynx, oropharynx, oral cavity and the hypopharynx.

In this context it is understood that the term "nasal airways" refers to the airways extending from the nostrils to the nasopharynx.

In this context it is understood that the term "endogenous gas" refers to gas produced within the body of a human.

In this context it is understood that the condition of the upper airways encompasses the absence or presence of one of the following: an inflammatory condition, an airway infection, common-cold, tumors, drug related effects, anatomical abnormalities, the patency of the sinus ostia, the size of the sinuses, the biochemical status of the sinuses, sinusitis affecting one or more sinuses, the location said sinusitis, the risk for developing sinusitis, the bacteriological status of the sinuses, or a combination thereof. In particular, the device is useful in the diagnosis of the conditions of the sinuses, e.g. the presence or absence of a pathological condition affecting the sinuses, and its location, such as primary cilliary dyskinesia (PCD) and cystic fibrosis (CF), nasal polyposis, allergic rhinitis, an inflammatory condition of the upper airways, a common cold, or a combination thereof.

According to one embodiment of the invention, the means for generating and/or maintaining an oscillating airflow sufficient to enhance the ventilation of the sinuses is a means for electronically or mechanically generating said airflow.

Preferably, said device is adapted to unilateral measurements, that is the measurement of the effect of an oscillating airflow on nasally exhaled gases, in one nostril at the time. This can be achieved either by using nasal olives, occluding one nostril while the measurement is performed in the other, or when using a mask, by occlusion of one nostril at the time.

According to another embodiment, the means for generating and/or maintaining an oscillating airflow is a means for registering the duration, frequency and/or volume of an oscillating airflow produced by the patient, e.g. by humming, comprising a feed-back mechanism, such as means for indicating to said patient that a pre-set necessary duration, frequency, flow and/or volume has been reached.

According to an embodiment of the present invention the oscillating airflow oscillates at a frequency between 1 to 1000 Hz, preferably between 10 to 1000 Hz, more preferably between 100 to 1000 Hz, and most preferably between 100 to 500 Hz.

According to another embodiment of the present invention the oscillating airflow oscillates at a frequency close to the resonance frequency of the paranasal sinuses.

According to another embodiment of the present invention the airflow is aspirated from the upper airways and the aspirator coupled to a sound generator that causes the air to oscillate.

According to a preferred embodiment of the present invention, said device is suitable for connection to a device for determining and recording the concentration and/or flow of a first gas present in the exhaled air of a human being, and a device for supplying a second breathing gas devoid of or containing minute amounts and/or a known amount of said first gas to said human being. Most preferably said first gas is nitric oxide and said second gas is a nitric oxide-free gas suitable for inhalation. One example of such a device is the NIOX® NO-analyser (Aerocrine AB, Solna, Sweden).

It is also possible to determine the concentration and/or flow of other gases, endogenous or exogenous. Examples of such gases include nitric oxide (NO), nitrogen, oxygen, carbon dioxide, carbon monoxide, and suitable inert gases, e.g. argon or xenon.

A further embodiment involves means for analysis of the time distribution of the NO, i.e. the shape of the curve when the concentration is plotted in relation to time and/or flow. This analysis will give information on the dynamic behavior of the sinuses and it is contemplated that this will make it possible to distinguish between degree and type of congestion, sinus volume, diameter of ostia, and to elucidate the possible pathology underlying the sinus problems under investigation in each particular patient The absolute amount of exhaled gas, e.g. NO, and its change over time, such as the increase, decrease, associated peak, slope and plateau values will reveal anatomical and physical differences. Using patient data collected from a number of patients, or data collected from measurements performed on the same patient at different occasions or using different frequency, flow and duration of the oscillating airflow, additional or more precise information can be gained. The following anatomical and physical differences are likely to be revealed using this approach:

ostium size/patency sinus volume sinus NO-production

NO-absorption

The present invention also makes available a method for the analysis of the condition of the upper airways of a human, in particular the sinus or sinuses of a human, wherein the concentration and/or flow of at least one gaseous component in nasally exhaled air is determined and recorded in the presence and absence of an oscillating airflow.

According to an embodiment of the present invention the oscillating airflow in the method of analysis oscillates at a frequency between 1 to 1000 Hz, preferably between 10 to 1000 Hz, more preferably between 100 to 1000 Hz, and most preferably between 100 to 500 Hz.

According to another embodiment of the present invention the oscillating airflow in the method of analysis oscillates at a frequency close to the resonance frequency of the paranasal sinuses.

According to another embodiment of the present invention the airflow in the method of analysis is aspirated from the upper airways and the aspirator coupled to a sound generator that causes the air to oscillate.

According to an embodiment of this method, the condition of the upper airways encompasses the absence or presence of one of the following: an inflammatory condition, an airway infection, common cold, tumors, drug related effects, anatomical abnormalities, the patency of the sinus ostia, the size of the sinuses, the biochemical status of the sinuses, sinusitis affecting one or more sinuses, the location said sinusitis, the risk for developing sinusitis, the bacteriological status of the sinuses, or a combination thereof. The present method is particularly suitable for determining the condition of the sinuses, such as the presence of absence of a pathological condition affecting the sinuses, such as primary ciliary dyskinesia (PCD) and cystic fibrosis (CF), nasal polyposis, allergic rhinitis, an inflammatory condition of the upper airways, or a combination thereof. The present invention thus makes available methods for use in the diagnosis of any one of these or related conditions/diseases.

According to another embodiment of this method, the condition of the upper airways is determined at at least two occasions, before and after the administration of a drug or the performance of a therapeutic intervention and the result is used to evaluate the effect of said drug or intervention.

The oscillating airflow necessary for the measurement can be achieved by urging the person undergoing the test or investigation, to produce an oscillating airflow simulating that achieved by humming. In that case, it may be necessary to include a feed-back function, i.e. to register the duration, frequency, flow and/or volume of this oscillating airflow produced by the patient, and indicating to said patient when a pre-set necessary duration, frequency, flow and/or volume has been reached.

The oscillating airflow can also be artificially produced and directed to the upper airways or a part thereof, e.g. to the sinus or sinuses.

According to one embodiment of the inventive method, the concentration and/or flow of a first gas present in the exhaled air of a human being is determined, while a second breathing gas devoid of or containing a minute and/or known amount of said first gas is, supplied to said human being. Preferably said first gas is nitric oxide and said second gas is a nitric oxide-free gas suitable for inhalation. One example of a device suitable for performing these functions is the NIOX® NO-analyser (Aerocrine AB, Solna, Sweden).

The method may also involve the determination of the concentration and/or flow of other gases, endogenous or exogenous. Examples of such gases include nitric oxide (NO), nitrogen, oxygen, carbon dioxide, carbon monoxide, and suitable inert gases, e.g. argon.

A further embodiment involves a step of analyzing the time distribution of the NO, i.e. the shape of the curve when the concentration is plotted in relation to time and/or flow. This analysis will give information on the dynamic behavior of the sinuses and it is contemplated that this will make it possible to distinguish between degree and type of congestion, sinus volume, diameter of ostia, and to elucidate the possible pathology underlying the sinus problems under investigation in each particular patient. The absolute amount of exhaled gas, e.g. NO, and its change over time, such as the increase, decrease, associated peak, slope and plateau values will reveal anatomical and physical differences. Using patient data collected from a number of patients, or data collected from measurements performed on the same patient at different occasions or using different frequency, flow and duration of the oscillating airflow, additional or more precise information can be gained. The following anatomical and physical differences are likely to be revealed using this approach:

ostium size (patency)
sinus volume
sinus NO-production
NO-absorption

A comparison of curves obtained when using the two-compartment model, in vivo measurements in the presence of an oscillating airflow, and measurements during silent nasal exhalation has been made. It is seen that, in the two-compartment model, the concentration of NO decreases as no new NO is produced in the syringe simulating the sinus (results not shown). In the in vivo tests, the curve exhibits a similar increase and peak (FIG. 1), although these values vary between the subjects tested. The decrease is however less, due to the replenishment of NO in the sinuses, and both the slope of the curve as well as the plateau level reached varies between the subjects tested.

This test has the obvious advantage of being non-invasive, rapid and objective. It will also be of interest to study if measurements during humming can be used to gain more information on conditions affecting the upper airways, and e.g. to better separate patients with nasal disorders and altered nasal NO release from healthy controls. Such disorders include e.g. CF, PCD, nasal polyposis and allergic rhinitis.

EXAMPLES

1. In Vivo Measurements 1.1 Healthy Controls

Characterization of Nasal NO During Humming

Ten healthy non-smoking volunteers (age 25-47 years, 6 males,) without any history of allergy, nasal disease, asthma or any other chronic lung conditions were recruited. Airway NO output was measured with a chemiluminescence system (NIOX®, Aerocrine AB, Stockholm, Sweden) designed to meet the ATS guidelines for exhaled NO (American Thoracic Society. *Am J Respir Crit Care Med* 1999; 160:2104-17). The analyzer was calibrated with standard gas mixtures of NO (987 parts per billion, AGA AB, Sweden). NO levels were measured during oral and nasal single breath exhalations. A tight fitting mask covering the nose was used for nasal measurements, and a mouthpiece was used for oral exhalations. The subjects started each maneuver by inhaling NO-free air through the nose and then exhaled at a fixed flow rate (0.20 L/s) for ten seconds either quietly or with nasal humming or oral phonation. The fixed flow rate was achieved by a dynamic flow restrictor in the analyzing system combined with a computerized visual feed back display of flow. The dynamic flow restrictor uses an elastic membrane valve to mechanically adjust flow rate and keep exhalation at 0.20 L/s within a wide range of exhalation pressures with minimal variation.

Nasal NO output during humming was calculated by subtracting the values obtained during silent nasal exhalations as described earlier (Lundberg et al., *Thorax* 1999; 54:947-952; Palm et al., *Eur Resp J* 2000; 16:236-41). NO release was calculated as the mean output (nl/min) during the last 80% of the exhalation.

To investigate if humming could exhaust the source of NO the subjects performed five consecutive humming maneuvers with different time intervals (5 seconds, 1 minute and 3 minutes) between each humming. Also, repeated silent nasal exhalations were performed at 5 sec intervals. Based on the results obtained from consecutive humming maneuvers (see below), all other humming in this study were preceded by a 3 minute period of silence.

Effects of NO Synthase Inhibition

In six of the subjects baseline nasal and oral NO measurements were made both during humming and silent exhalations. Then either a solution of NG-L-arginine methyl ester (L-NAME) (Sigma, Poole, UK.) 15 mg (2.2 mM) in 2.5 ml of saline or saline alone was delivered in random order through both nostrils by a jet nebulizer (Devilbiss, Somerset, Pa., USA) and the NO measurements were repeated 20 min. after application of the solutions.

Effects of Flow, Pressure and Frequency During Humming

To compare the results from the model described above to the in vivo situation we performed additional experiments in five of the subjects. They were asked to exhale in turn at two fixed flow rates (0.20 and 0.25 L/s) against no resistance or at a resistance of 50 cm $H_2O$ $L^{-1}$ $s^{-1}$ for a period of ten seconds either silently or with nasal humming or oral phonation. This was followed by nasal humming maneuvers at three different sound frequencies. Frequency was registered with the microphone taped on the neck of the subject. NO output was calculated from the mean concentration during the entire exhalation.

Results

Figure 1:
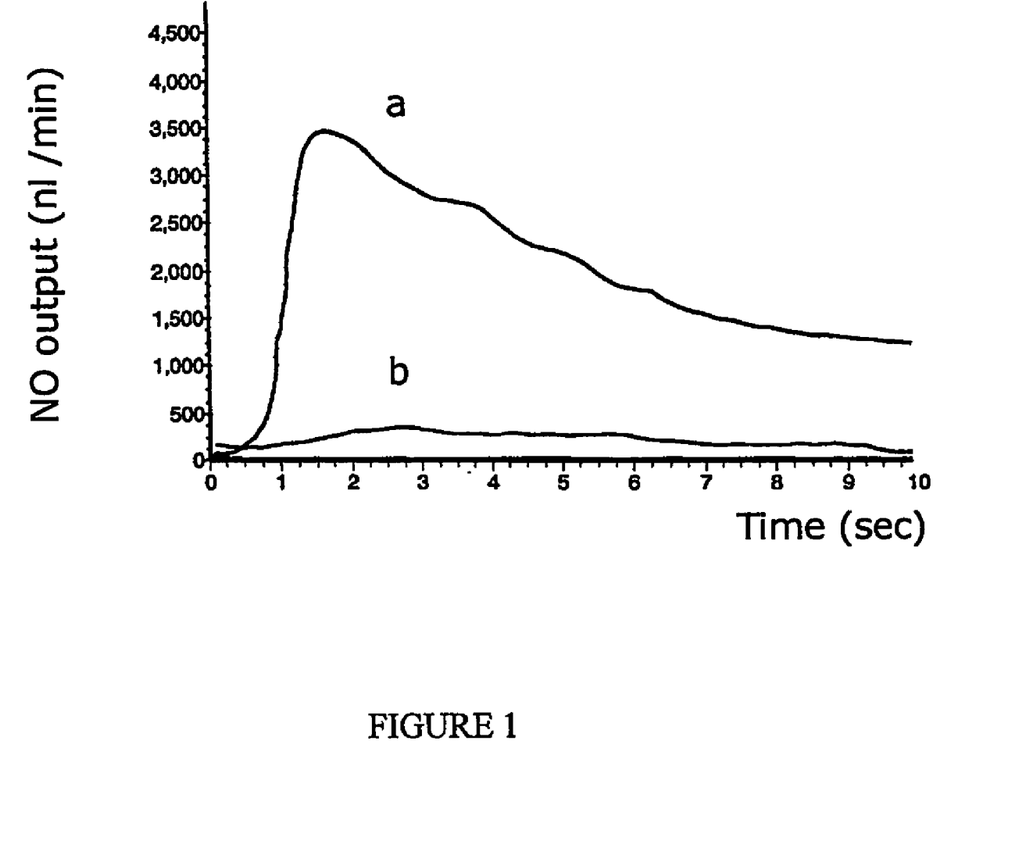
FIG. 1 shows an original tracing of NO during a single breath nasal exhalation with humming (a) or silently (b)

In all humming experiments an initial NO peak was observed followed by a progressive decline (FIG. 1). Total nasal NO output increased during humming as compared to silent exhalation (from 471±73 nL/min during silent exhalation to 2233±467 nL/min during humming; p<0.001) (FIG. 1). Orally exhaled NO was 144±20 nL/min with silent exhalation and 152±20 nL/min with phonation (p=0.22).

Figure 2:
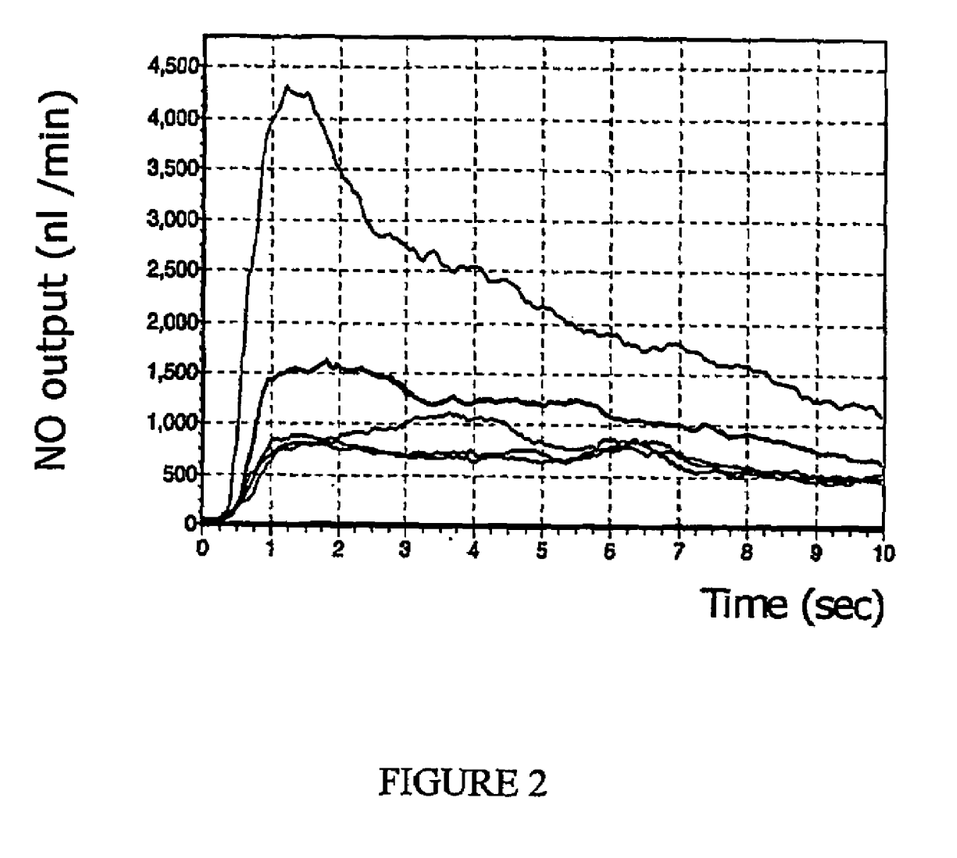
FIG. 2 shows the effect of repeated humming maneuvers on nasal NO output. Five consecutive exhalations with humming were performed at 5 seconds intervals. A progressive reduction in NO levels was observed after each maneuver until a plateau was reached.
Figure 3:
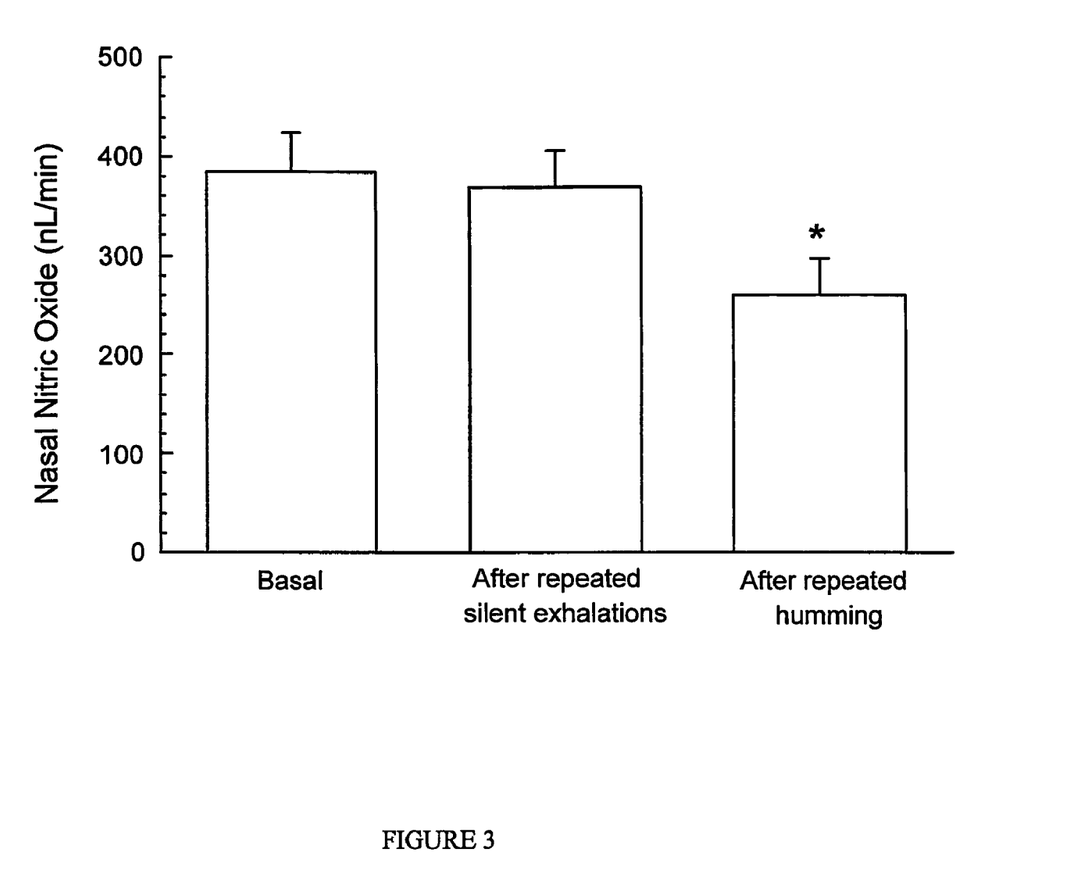
FIG. 3 shows the nasal NO output measured during a silent exhalation at baseline, immediately after repeated silent nasal exhalations and immediately after repeated humming maneuvers (five consecutive 10 s nasal exhalations with humming). *=p=0.002 compared to baseline, n=6.
Figure 4:
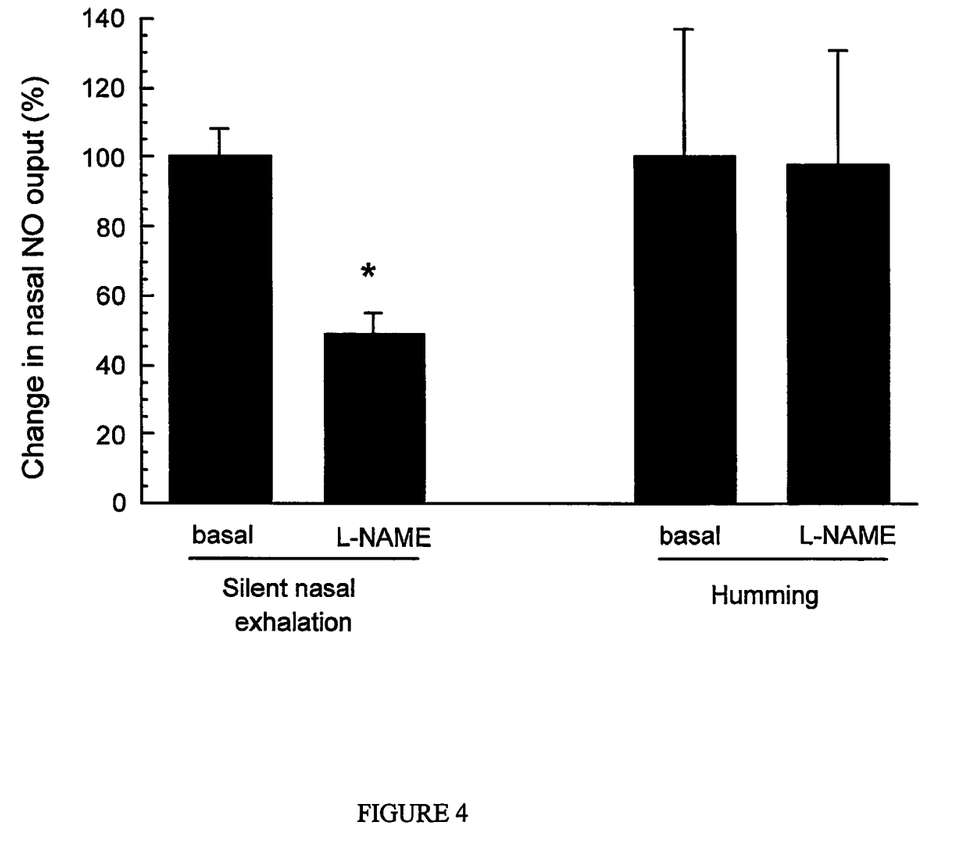
FIG. 4 shows the change in nasal NO output (%) after topical nasal application of an NO synthase inhibitor (L-NAME). The subjects exhaled either silently or with humming. (*p=0.002, n=6)

NO output measured during five single-breath humming maneuvers with 3 minutes intervals between each humming was similar showing an intra-individual variability of less than 15%. With one minute intervals the intra individual variability was nearly 70%. With 5 seconds intervals NO decreased progressively after each maneuver until a stable plateau was reached at a level of 571±88 nL/min compared to levels during the first humming of 2233±467 nL/min, p=0.002 (FIG. 2). In all subjects the low plateau was reached within four nasal humming maneuvers. In contrast, five consecutive silent nasal exhalations with 5 sec intervals did not affect NO output (FIG. 3). However, silent nasal NO output measured immediately after repeated humming maneuvers was lower than basal silent NO in all subjects (261±35 nL/min vs 384±39 nL/min; p=0.021). There was a substantial variability in the reduction of silent nasal NO after consecutive humming ranging between 5-50%. Topical application of L-NAME reduced silently exhaled nasal NO levels by more than 50% from 392±33 nL/min to 194±24 nL/min; p=0.002 (FIG. 4). In contrast, the humming-induced increase in NO output was not affected (2417±894 nL/min before L-NAME vs 2368±811 nL/min after L-NAME, p=0.77).

Increasing the exhalation flow rate during humming from 0.20 to 0.25 L/s resulted in higher nasal NO output (from 807±172 to 1074±197 ni/min, p<0.05).

Change of humming frequency also affected nasal NO output. NO levels were 940±77 nL/min at 130 Hz, 807±77 nL/min at 150 Hz and 719±58 nL/min at 450 Hz (p<0.05). NO output increased with higher nasal pressure during humming (from 807±77 nL/min at 1 cm H2O to 932±26 nL/min at 10 cm H2O, p>0.05).

1.2 Sinus Volume

A preliminary study involving two healthy subjects, for whom the sinus volumes were previously recorded, was performed. The level of nasally exhaled NO was determined during silent breathing and during humming, using a standardised chemiluninescence system (NIOX®, Aerocrine AB, Solna, Stockholm) as above. The NO-values recorded during silent breathing were approximately the same. The peak NO-value for the subject having a larger sinus volume was however considerably higher (about 1500 ppb) than for the subject having a smaller sinus volume (300 ppb). In the subject having larger sinus volume, the NO-value decreased more slowly. The results indicate that an analysis of the peak, slope and plateau values can give information on anatomical and physiological features of the upper airways, and in particular the sinuses. (Results not shown.)

1.3 Correlation to Sinus Problems

Ten healthy non-smoking subjects (age 25-52 years, 5 males) without any history of allergy or chronic airway disorder and 10 patients with chronic sinusitis and nasal polyposis (age 30-56 years, 5 males) took part in the study. None of the controls had any ongoing respiratory tract infection at the time of the study. The patients were on a waiting list for sinus surgery. All had bilateral polyps and completely opaque sinuses according to a previous CT scan. All were on treatment with topical nasal corticosteroids, three had concomitant asthma and four had aspirin intolerance. NO was measured in nasal single-breath exhalations using a chemiluminescence system developed to meet the criteria of the ATS guidelines for exhaled NO measurements (Aerocrine AB, Stockholm, Sweden). A tight fitting mask covering the nose was used and the subjects exhaled nasally with closed mouth at a fixed flow rate (0.10 l/s) for 10 s either silently or with humming. NO levels were calculated as the mean output (nl/min) during the last 80% of the exhalation. Exhalation flow rate was monitored and variation was minimal (<0.02 l/s).

Results

Figure 5:
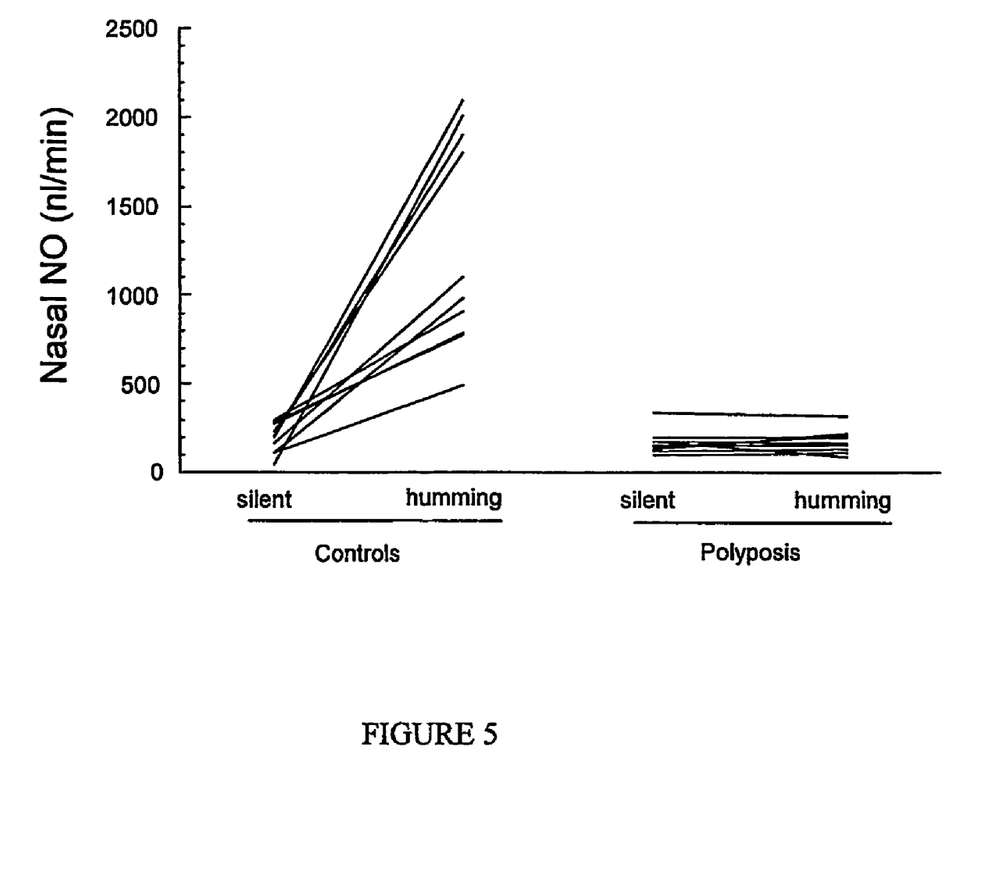
FIG. 5 shows the effect of silent nasal exhalation or humming on nasal NO output in controls and patients with nasal polyposis.

During quiet exhalation nasal NO was similar in controls and patients (189±27 nl/min vs 162±22 nl/min). Nasal NO increased 7-fold during humming (to 1285±189 nl/min) in controls but remained completely unchanged in the patients (169±21 nl/min, FIG. 5).

It was shown that the increase in nasal NO during humming is completely absent in patients with nasal polyposis. The most likely explanation is a lack of air-passage between the sinuses and the nasal cavity. Interestingly, one of the patients had surgery during the course of this study and in this patient nasal NO increased during humming to almost normal levels two weeks after the operation (data not shown).

2. Two-compartment Model Study—the Sinus/Nasal Model

Description of the Model

Figure 6:
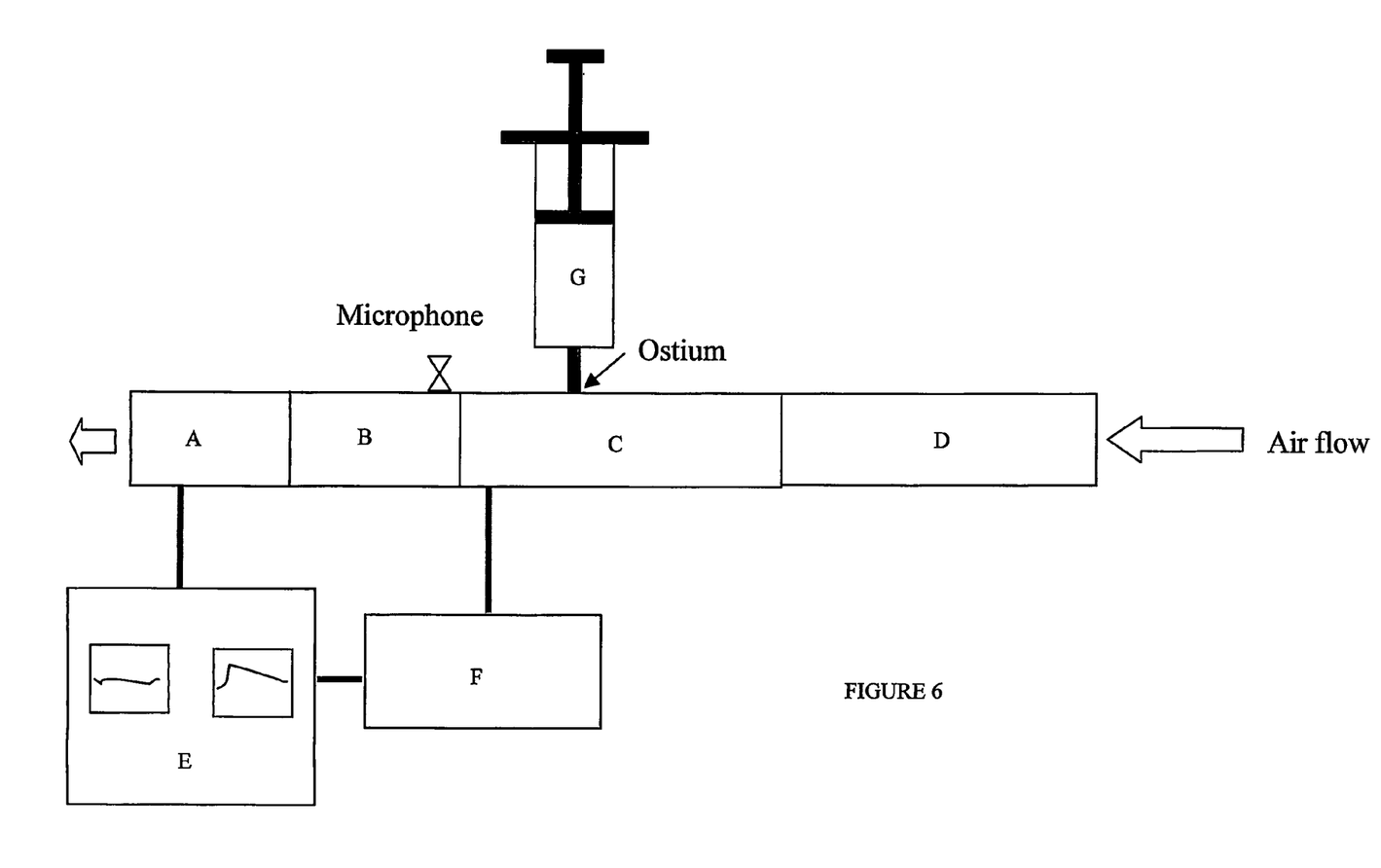
FIG. 6 is a schematic presentation of an experimental model of the sinus (G), the ostium (syringe tip) and the nasal cavity (C). A denotes the flow/pressure meter, B denotes the flow resistor, D denotes the sound generator (rubber duck call), E denotes the display, and F denotes the NO analyzer.

NO output was measured in a two-compartment model resembling the nasal cavity and one sinus (FIG. 6). A syringe (representing the sinus) was filled with various NO gas concentrations ranging between 2 and 10 ppm (AGA AB, Sweden), and connected horizontally to a plastic cylinder (representing the nasal cavity) via a Luer fitting. The diameter of the syringe tip (representing the ostium) was varied between 0.8 to 4.0 mm. The volume of the syringe was varied between 5 and 20 ml. The distal end of the cylinder (nasal cavity) was left open or connected to a Hans Rudolph resistor of 50 cm $H_2O$ $L^{-1}$ $s^{-1}$ thereby generating cylinder pressures of either 1 or 10 $cmH_2O$. Flow and pressure were measured by a linear pneumotachymeter (Hans Rudolph Inc). Resulting NO levels were measured at the distal end of the cylinder by a rapid-response chemiluminescence system (Aerocrine AB, Stockholm, Sweden). The signal output from these devices were connected to a computer-based system (Aerocrine NO system, Aerocrine AB, Stockholm, Sweden) and yielded an instant on-screen display of flow, pressure, NO concentration and NO output.

Artificial Generation of Humming in the Model

Pressurized NO-free air was set to generate three different flow rates (0.20, 0.25 and 0.30 L/s). The air was led through the plastic cylinder (nasal cavity) either via a rubber duck call (Hudson & Co, UK), which yielded a pulsating airflow or via a rubber duck call without the sound generating membrane (quiet control). Three duck calls with different fundamental frequencies (120, 200 and 450 Hz) were used. NO was measured during a ten sec period and all experiments were repeated five times. In an additional experiment, a turbulent flow was generated by leading pressurized NO-free air through a plastic mesh connected to the cylinder and NO was measured as described above. This experiment was done without a sound generating device.

In a separate experiment we studied the effect of 3 different humming frequencies (120, 200 and 450 Hz) on NO output from sinuses with different resonance frequencies (120 or 200 Hz).

Human Humming in the Model

In the same model the pulsating airflow was also generated by a subject performing oral exhalation through the cylinder with or without phonation at two fixed flow rates (0.20 or 0.25 L/s) and three different frequencies (130, 150 or 450 Hz). NO output was calculated from the entire exhalation (10 sec) with subtraction of oral NO output. All experiments were repeated five times. To estimate the rate of air exchange between the two cavities, we also measured the remaining NO concentration in the syringe at the end of each experiment.

Measurement of Artificial and Human Humming Sound Frequency.

The audio signal of humming was picked up by a TCM 110 Tiepin electret condenser microphone placed on the plastic cylinder in the model (FIG. 6) and recorded directly onto a PC by the Soundswell Signal Workstation. The fundamental frequency was extracted by its Corr module that computes the autocorrelation of the audio signal in two adjacent time windows. The mean fundamental frequency and standard deviation were then determined by means of its histogram module.

The resonance frequency of the model system was calculated according to Durrant and Lovrinic (*Bases of Hearing Science*, 3$^{rd}$ Ed., Williams and Wilkins, Baltimore, 1995: 60).

Results

In the standard setting of the model we used a fixed flow rate of 0.2 L/s, an NO concentration of 8 ppm, a pressure of 1 cm $H_2O$, a syringe volume of 15 ml, an ostium size of 1.9 mm and a humming frequency of 200 Hz. The resonance frequency of this system was calculated to be 200 Hz. When changing one parameter in the experiments all other values were kept constant.

In all experiments using the model, artificial and human humming caused an increase in NO output compared to silent exhalation. When using artificial humming in the model NO output increased >10-fold from 23.7±0.1 nL/min during silent airflow to 295±4.5 nL/min during humming (p<0.05). When a subject was humming in the model NO output increased from 27.7±0.1 nL/min during silent exhalation to 175±8 nL/min (p<0.05). No difference in NO output was seen in the model when using a turbulent flow compared to a non turbulent flow (25.2±0.2 nL/min and 23.7±0.1 nL/min, respectively).

Effect of Ostium Size

Figure 7:
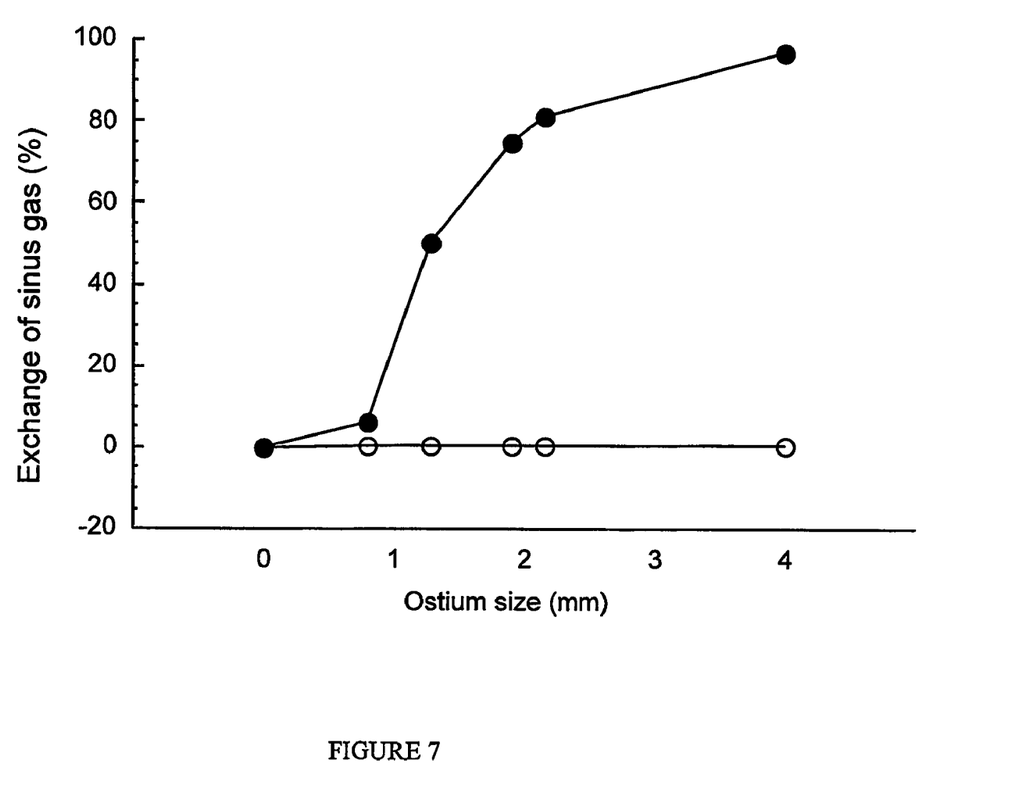
FIG. 7 shows the influence of ostium size on sinus gas exchange in the experimental model. A subject performed a single breath exhalation at a fixed flow rate (0.2 L/sec) either silently (unfilled) or with phonation (filled). Sinus gas exchange was calculated by measuring NO in the syringe before and immediately after each exhalation.

Ostial diameters of 0.8, 1.29, 1.9, 2.1 and 4.0 mm were used. NO output during humming increased with larger ostium size (FIG. 7). With a ratio for the ostium size of 1:1.6:2.4:2.6:5 the ratios for NO output in the human and artificial models were 1:4.5:6:14:30 and 1:8:13:15:39 respectively. As an estimation of the rate of air exchange in the sinus, the remaining NO concentration in the syringe was measured immediately after the exhalations (FIG. 7). We found no significant changes in syringe NO concentrations after silent exhalations regardless of ostium size. In contrast, during humming the air exchange was strongly dependent on ostium size and reached almost 100% with the largest ostium (FIG. 7).

Effect of Humming Frequency

Figure 8:
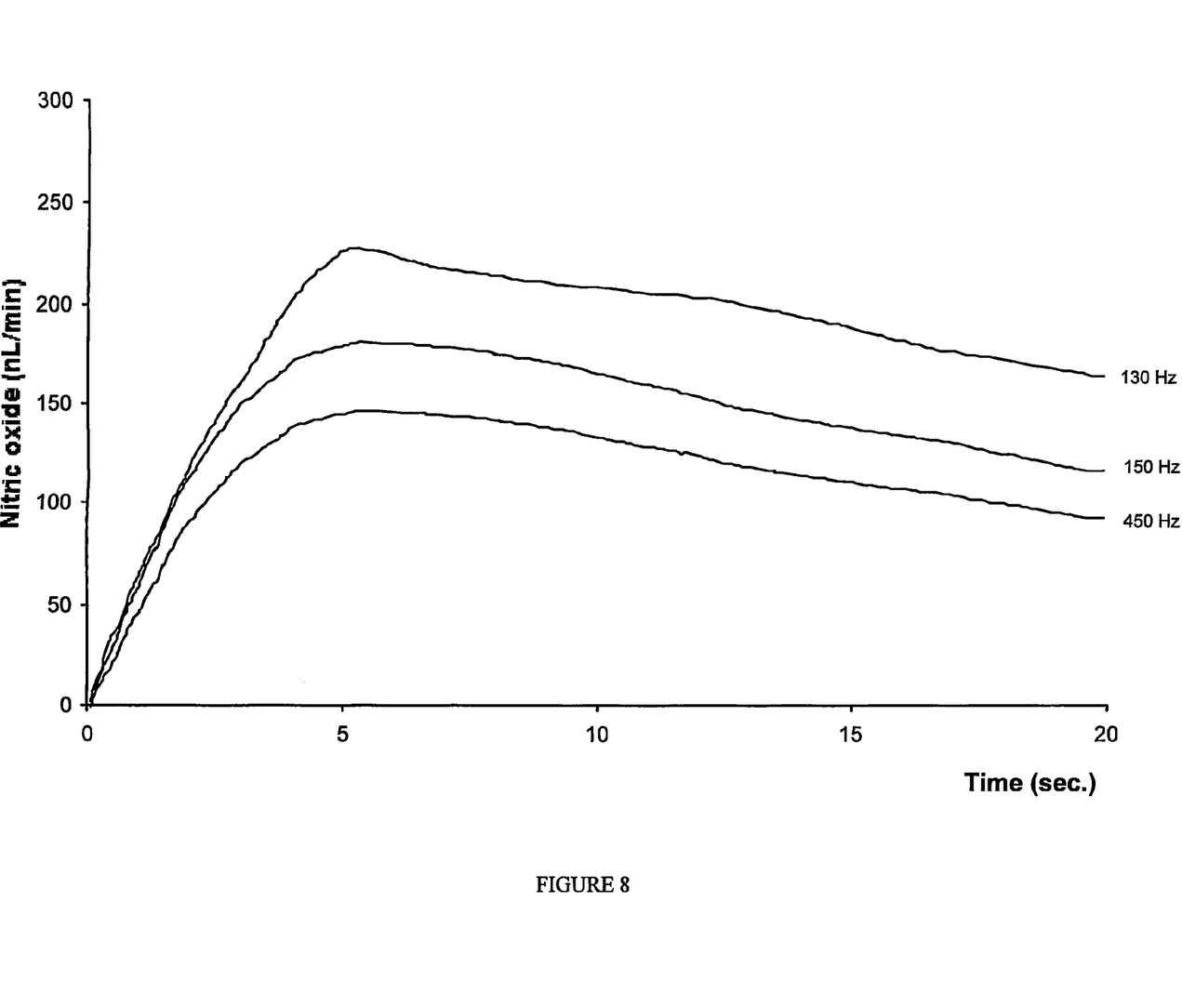
FIG. 8 shows the effect of three different humming frequencies on NO levels in a sinus/nasal model. A subject exhaled orally in the model at a fixed flow rate of 0.2 L/s, a NO concentration of 8 ppm, a resistance of 1 cmH$_2$O and an ostium size of 1.9 mm.

We found significant changes in NO output by modifying the frequency of humming in all experiments. When using artificial humming in the model NO output was 230±5.7 nL/min at a frequency of 120 Hz, 295±3.4 nL/min at 200 Hz, and 143±2.0 nL/min at 450 Hz (p<0.05, FIG. 8).

In the human humming model NO levels were 204±11 nL/min at 130 Hz, 175±8 nL/min at 150 Hz and 143±2 nL/min at 450 Hz (p<0.05, n=5). When studying the effect of different humming frequencies on NO output from syringes with different resonance frequencies we found that the NO output was greatest when the humming frequency was close to the resonance frequency of the particular sinus (Table I).

TABLE I

Effect of humming frequency on NO output (nL/min) using sinuses with different resonance frequency in the model.

| | Sinus Resonance Frequency | |
|---|---|---|
| Humming Frequency | 120 Hz | 200 Hz |
| 120 Hz | 1043 ± 10 | 527 ± 5.8 |
| 200 Hz | 561 ± 8.3 | 611 ± 7.7 |
| 400 Hz | 286 ± 6.3 | 418 ± 8.1 |

Effect of Syringe Volume

Table II and III show the result after humming when the ostial size, NO concentration, flow and resistance were kept constant according to the standard setting. Syringe volumes of 5, 10, 15 and 20 ml were used. With a ratio for the sinus volumes of 1:2:3:4 the ratios for NO levels were 1:2.5:5:7 in the artificial humming model and 1:2:4:5.5 in the human humming model.

Effect of Syringe NO Concentration

Table II and III show the effect of syringe NO concentration during humming. The NO concentrations of 2, 4, 8 and 10 ppm were used. With a ratio for the syringe NO concentration of 1:2:4:5 the ratios for NO levels in the artificial and human humming models were respectively 1:2.1:4:5.5 and 1:2:3:7.

Effect of Airflow Rate

Results concerning NO output at different nasal flow rates during humming are shown in table II and III. With a ratio for the flow rate of 1:1.25:1.5 the ratios for NO levels in the artificial and human humming models were 1:1.25:1.4 and 1:1.5:2 respectively.

TABLE II

The influence of sinus volume, sinus NO concentration and flow rate on resulting NO levels induced by an artificial pulsating airflow in a model of the nose and sinus (for details see methods).

| | | Artificial humming NO output (nL/min) |
|---|---|---|
| Sinus Volume | 5 ml | 79 ± 1.0 |
| | 10 ml | 159 ± 4.5* |
| | 15 ml | 295 ± 3.4* |
| | 20 ml | 427 ± 3.7* |
| NO concentration | 2 ppm | 76 ± 1.5 |
| | 4 ppm | 162 ± 2.8* |
| | 8 ppm | 295 ± 3.4* |
| | 10 ppm | 434 ± 6.1* |
| Flow | 0.20 L/sec | 295 ± 3.4 |
| | 0.25 L/sec | 369 ± 5.8* |
| | 0.30 L/sec | 411 ± 7.6* |

*= p < 0.05

TABLE III

The influence of sinus volume, sinus NO concentration and flow rate on resulting NO levels induced by human pulsating airflow in a model of the nose and sinus (for details see methods).

| | | Human humming NO output (nL/min) |
|---|---|---|
| Sinus Volume | 5 ml | 79 ± 1.0 |
| | 10 ml | 87 ± 3.6* |
| | 15 ml | 175 ± 8.0* |
| | 20 ml | 242 ± 14.7* |

TABLE III-continued

The influence of sinus volume, sinus NO concentration and flow rate on resulting NO levels induced by human pulsating airflow in a model of the nose and sinus (for details see methods).

|  |  | Human humming NO output (nL/min) |
|---|---|---|
| NO concentration | 2 ppm | 57 ± 8.1 |
|  | 4 ppm | 118 ± 14.6* |
|  | 8 ppm | 175 ± 8.0* |
|  | 10 ppm | 416 ± 32* |
| Flow | 0.20 L/sec | 175 ± 8.0 |
|  | 0.25 L/sec | 268 ± 4.8* |
|  | 0.30 L/sec | 356 ± 10* |

*= $p < 0.05$

Effect of Pressure

In the artificial humming model we found an increase in NO output with higher pressure during humming (from 175±8 nL/min to 377±22 nL/min). In the human humming model we found a reduction as we increased the pressure (from 250±3.4 nL/min to 140±1.9 nL/min).

3. Statistics

The NO output was calculated for all sampling modalities as flow x NO concentration. Non-parametric statistics with two-way p values were used. For analysis of paired data Friedman's test and Wilcoxon's test were used. A p value less than 0.05 was considered significant. Results are given as mean±SEM.

4. Discussion

The large and reproducible increase in nasal NO caused by humming in healthy volunteers has been characterized, as well as in a model of the nose and sinus. The humming method gives relevant information about the relative contribution of NO from the nose and sinus as well as ostium patency. Several factors strongly indicate that the NO increase seen during humming is due to a rapid washout of NO accumulated in the paranasal sinuses. The profiles of the nasal exhalation curves (peak and progressive decline) in the model and in the human studies were very similar and the factors influencing NO levels were identical. Both the peak and the total nasal NO output were markedly decreased following repeated consecutive humming manouvers and a complete recovery was observed after a 3 minute period of silence. Again, this pattern fits well with the notion that humming empties the sinuses and that a period of silence will allow for NO to accumulate again. A NOS inhibitor (L-NAME) applied locally in the nose reduced silent nasal NO levels by 50% but had no effect on the increase during humming. Assuming that this route of administration mostly affects the nasal mucosa with a less penetration into sinuses, this also supports a sinus origin of nasal NO during humming.

Ostium size seemed to be the most important factor affecting the increase in nasal NO during humming. Sinus NO concentrations and humming frequency also affected sinus ventilation. Interestingly, the humming frequency affected sinus output both in the model and in the healthy volunteers. These preliminary experiments have shown that the ventilation of the sinus in the model is greatest when the humming frequency is close to the resonance frequency of the sinus model.

From the experiments looking at remaining NO in the syringe after single-breath exhalations it is obvious that humming is an enormously effective means of increasing sinus ventilation. This is also supported by the in vivo experiments where the rapid decline in NO during humming indicated sinus emptying. The results show that almost the entire sinus volume is exchanged in one single exhalation if the subject is humming. Even when using a small ostial diameter humming was very effective in ventilating the sinus in the model used. This suggests that humming could help to increase sinus ventilation in patients with sinusitis and partly obstructed ostia.

In the present study silent nasal NO levels were between 5 to 50% lower immediately after repeated humming. If we assume that the sinuses are effectively emptied by this maneuver, the decrease should fairy well reflect the normal contribution from the sinuses to NO found in nasally exhaled air. It is however important to note that this assumption may be true only under the exact conditions of this study. Nevertheless using the methods described here, it may be possible to better separate sinus NO from nasal mucosal NO release.

Although the invention has been described with regard to its preferred embodiments, which constitute the best mode presently known to the inventors, it should be understood that various changes and modifications as would be obvious to one having the ordinary skill in this art may be made without departing from the scope of the invention as set forth in the claims appended hereto.

The invention claimed is:

1. A device for use in diagnosis of a condition of the upper airways in a human, wherein said device comprises means for generating and/or maintaining an oscillating airflow in said upper airways or parts thereof; said device being suitable for connection to means for determining and recording the concentration and/or flow of nitric oxide (NO) present in exhaled air of said human; and wherein the condition of the upper airways is an absence or presence of a condition selected from the group consisting of an inflammatory condition, an airway infection, a common cold, a tumor, a drug related effect, an anatomical abnormality, a patency of the sinus ostia, a size of the sinuses, a biochemical status of the sinuses, a sinusitis affecting one or more sinuses, a location of said sinusitis, a risk for developing sinusitis, a bacteriological status of the sinuses, and a combination thereof.

2. A device according to claim 1, wherein the means for generating and/or maintaining an oscillating airflow comprises means for electronically or mechanically generating said airflow.

3. A device according to claim 1, wherein the means for generating and/or maintaining an oscillating airflow comprises means for registering a duration, frequency and/or volume of an oscillating airflow produced by a patient coupled to a means for indicating to said patient that a pre-set necessary duration, frequency and/or volume has been reached.

4. A device according to claim 1, wherein the oscillating airflow oscillates at a frequency between 1 to 1000 Hz.

5. A device according to claim 1, wherein the oscillating airflow oscillates at a frequency between 10 to 1000 Hz.

6. A device according to claim 1, wherein the oscillating airflow oscillates at a frequency between 100 to 1000 Hz.

7. A device according to claim 1, wherein the oscillating airflow oscillates at a frequency between 100 to 500 Hz.

8. A device according to claim 1, wherein the oscillating airflow oscillates at a frequency close to a resonance frequency of the paranasal sinuses.

9. A device according to claim 1, wherein said device comprises means for unilaterally diagnosing an abnormal state affecting only the right or left hand side of the nasal airways including paranasal sinuses.

10. A device for use in diagnosis of a condition of the upper airways in a human, wherein said device comprises means for generating and/or maintaining an oscillating airflow in said upper airways or parts thereof and means for determining and recording a concentration and/or flow of nitric oxide (NO) present in exhaled air of said human, and means for supplying a breathing gas devoid of or containing only minute and/or known amounts of NO to said human.

11. A device according to claim 10, wherein said breathing gas is a nitric oxide-free gas suitable for inhalation.

12. A device according to claim 10, wherein said device is suitable for connection to means for determining and recording a concentration and/or flow of a tracer gas.

13. A device according to claim 10, wherein said device is suitable for connection to means for determining and recording the concentration and/or flow of a tracer gas, said tracer gas being an endogenous gas.

14. A device according to claim 10, wherein said device is suitable for connection to means for determining and recording a concentration and/or flow of a tracer gas, said tracer gas being an exogenous gas.

15. A method for diagnosing a condition of the upper airways in human comprising:
determining a concentration and/or a flow rate of at least one gaseous component in a sample of nasally exhaled air in the presence and absence of an oscillating airflow acting on the upper airways or parts thereof, wherein the condition of the upper airways is the absence or presence of a condition selected from the group consisting of an inflammatory condition, an airway infection, a common cold, a tumor, a drug related effect, an anatomical abnormality, a patency of the sinus ostia, a size of die sinuses, a biochemical status of the sinuses, sinusitis affecting one or more sinuses, a location of said sinusitis, a risk for developing sinusitis, a bacteriological status of the sinuses, or a combination thereof; and
calculating the mean output of the gaseous component.

16. A method according to claim 15, wherein the oscillating airflow oscillates at a frequency between 1 to 1000 Hz.

17. A method according to claim 15, wherein the oscillating airflow oscillates at a frequency between 10 to 1000 Hz.

18. A method according to claim 15, wherein the oscillating airflow oscillates at a frequency between 100 to 1000 Hz.

19. A method according to claim 15, wherein the oscillating airflow oscillates at a frequency between 100 to 500 Hz.

20. A method according to claim 15, wherein the oscillating airflow oscillates at a frequency close to a resonance frequency of sinus cavities.

21. A method according to claim 15, wherein said human is urged to produce the oscillating airflow simulating an oscillation achieved during humming.

22. A method according to claim 15, wherein the oscillating airflow is artificially produced and directed to the upper airways of parts thereof.

23. A method for diagnosing a condition of the upper airways in a human comprising:
determining a concentration and/or a flow rate of nitric oxide (NO) present in a sample of exhaled air by a human in the presence and absence of an oscillating airflow acting on the upper airways or parts thereof, while a breathing gas devoid of or containing minute and/or known amounts of said NO has been supplied to said human; and
calculating the mean output of NO.

24. A method according to claim 23, wherein said breathing gas is a nitric oxide-free gas suitable for inhalation.

25. A method according to claim 23, wherein the concentration and/or flow of an endogenous gas in nasally exhaled air is determined in the presence and in the absence of said oscillating airflow acting on the upper airways.

26. A method according to claim 23, wherein an exogenous gas is administered to the human and the concentration and/or flow of said gas in nasally exhaled air is determined in the presence and in the absence of said oscillating airflow acting on the upper airways.

27. A method according to claim 23, wherein the condition of the upper airways is the absence or presence of a condition selected from the group consisting of an inflammatory condition, an airway infection, a common cold, a tumor, a drug related effect, an anatomical abnormality, a patency of the sinus ostia, a size of the sinuses, a biochemical status of the sinuses, sinusitis affecting one or more sinuses, a location of said sinusitis, a risk for developing sinusitis, a bacteriological status of the sinuses, or a combination thereof, and wherein the upper airways, nasal airways and paranasal sinuses are subjected to unilateral study by analyzing nasally exhaled air first from one nostril and then from the other nostril.

28. A method according to claim 15, wherein the condition of the upper airways is determined on at least two occasions, including before and after administration of a drug or performance of a therapeutic intervention in order to evaluate the effect of said drug or intervention.

29. A method according to claim 24, wherein the condition of the upper airways is determined on at least two occasions, including before and after administration of a drug or performance of a therapeutic intervention in order to evaluate the effect of said drug or intervention.

* * * * *

UNITED STATES PATENT AND TRADEMARK OFFICE
CERTIFICATE OF CORRECTION

| | | |
|---|---|---|
| PATENT NO. | : 7,270,638 B2 | Page 1 of 1 |
| APPLICATION NO. | : 10/496897 | |
| DATED | : September 18, 2007 | |
| INVENTOR(S) | : Jon Lundberg et al. | |

It is certified that error appears in the above-identified patent and that said Letters Patent is hereby corrected as shown below:

In Claim 15, column 15, line 40, replace "a size of die sinuses" with --a size of the sinuses--.

In Claim 22, column 16, line 9, replace "airways of parts thereof" with --airways or parts thereof--.

Signed and Sealed this

Eighth Day of July, 2008

JON W. DUDAS
*Director of the United States Patent and Trademark Office*